(12) United States Patent
Ricker (10) Patent No.: US 12,383,431 B2
(45) Date of Patent: Aug. 12, 2025

(54) VENTILATED PROTECTIVE EYEWEAR SYSTEMS, DEVICES, AND METHODS

(71) Applicant: Jorli Ricker, Furry Creek (CA)

(72) Inventor: Jorli Ricker, Furry Creek (CA)

(*) Notice: Subject to any disclaimer, the term of this patent is extended or adjusted under 35 U.S.C. 154(b) by 0 days.

(21) Appl. No.: 18/774,769

(22) Filed: Jul. 16, 2024

(65) Prior Publication Data

US 2025/0082505 A1  Mar. 13, 2025

Related U.S. Application Data (63) Continuation of application No. 18/668,018, filed on May 17, 2024, now abandoned.

(60) Provisional application No. 63/581,887, filed on Sep. 11, 2023.

(51) Int. Cl.
*A61F 9/02* (2006.01)

(52) U.S. Cl.
CPC .............. *A61F 9/028* (2013.01); *A61F 9/026* (2013.01)

(58) Field of Classification Search
CPC ............ A61F 9/02; A61F 9/026; A61F 9/028
See application file for complete search history.

(56) References Cited

U.S. PATENT DOCUMENTS

| | | | | |
|---|---|---|---|---|
| 4,707,863 A * | 11/1987 | McNeal | ............. | A61F 9/028 2/439 |
| 5,363,512 A * | 11/1994 | Grabos, Jr. | ............. | A61F 9/028 2/441 |
| 5,689,834 A * | 11/1997 | Wilson | ............. | A61F 9/028 2/435 |
| 6,029,271 A * | 2/2000 | Banuchi | ............. | A61F 9/04 2/9 |
| 6,481,845 B1 * | 11/2002 | Gazzara | ............. | A61F 9/026 351/158 |
| 7,137,153 B2 * | 11/2006 | Hussey | ............. | A61F 9/028 2/437 |
| 9,009,874 B2 * | 4/2015 | McNeal | ............. | A61F 9/028 2/435 |
| 9,138,026 B2 * | 9/2015 | Sandor | ............. | A41D 13/00 |
| 10,751,218 B2 * | 8/2020 | Blanchard | ............. | A61F 9/028 |
| 2011/0296596 A1 * | 12/2011 | Chen | ............. | A61F 9/028 2/436 |
| 2018/0289548 A1 * | 10/2018 | Wang | ............. | A61F 9/028 |
| 2023/0072304 A1 * | 3/2023 | Young | ............. | A61F 9/025 |

* cited by examiner

*Primary Examiner* — F Griffin Hall
(74) *Attorney, Agent, or Firm* — C. Brandon Browning; Maynard Nexsen PC (57) ABSTRACT

A goggle device is disclosed that comprises a frame, a lens attached to a frame, and a sealing component attached to the frame and configured to seal against a face of a user. A space between the lens and the face of the user defines an interior volume of the goggle. The frame includes a plurality of apertures that provide for ventilation through the sealing component of the goggle. The plurality of apertures can be disposed between the external environment and the sealing component. The disclosed goggle devices provide an additional pathway for moisture to leave the sealing component of the goggle thereby reducing the wetting and sponging effect that occurs in the sealing component from physical exertion of the user as well as allowing airflow to dry the sealing component of the goggle thereby reducing condensation on the lens and improving optical clarity.

23 Claims, 6 Drawing Sheets

VENTILATED PROTECTIVE EYEWEAR SYSTEMS, DEVICES, AND METHODS

CROSS-REFERENCE TO RELATED APPLICATION

This application is a continuation of and claims priority to U.S. Non-provisional application Ser. No. 18/668,018, entitled "VENTILATED PROTECTIVE EYEWEAR SYSTEMS, DEVICES, AND METHODS" filed on May 17, 2024 and U.S. Provisional Application No. 63/581,887, entitled "VENTILATED PROTECTIVE EYEWEAR SYSTEMS, DEVICES, AND METHODS" and filed on Sep. 11, 2023, which is incorporated herein by reference in its entirety.

FIELD

The present disclosure generally relates to a method of improving the ventilation characteristics of protective eyewear.

BACKGROUND

Many activities require a conscientious participant to use personal protective equipment designed to protect the physical health of the wearer's eyes while providing clear vision in a variety of environments.

In humid environments and/or during strenuous activity, it is common for the lens of protective eyewear to accumulate moisture in the form of condensation. This condensation impedes clear vision through the eyewear creating inconvenience and or danger to the wearer. A form of eye protection commonly referred to as a goggle includes a seal around its perimeter acting as a barrier to dust and or other contaminants. A primary contributor to condensation on the lens of a goggle is the humidity trapped inside the air volume of the goggle as well as moisture held in the components of the goggle, namely the element which seals the goggle to a wearer's face, which can absorb perspiration and transfer additional moisture into the volume of the goggle. Common solutions to this problem of condensation on the lens focus on improving the ability for fresh air to enter the lens and displace the moist air. Commonly a goggle is sealed to the wearer's face using an open cell, reticulated, polyether foam material. This material is primarily intended to provide a comfortable fit across a variety of face shapes while also acting as a barrier to dust and other particulates. The nature of this open cell foam allows air to travel through somewhat, but the foam is typically adhered to a solid surface on the frame of a goggle, while also being compressed by the tension in a head strap against the user's face on another side. This arrangement restricts the flow of air through the face foam.

The present invention improves upon the common ventilation scheme by providing a path from the user's face for an air exchange to the exterior of the goggle through the surface on which the face foam is adhered.

SUMMARY

According to embodiments consistent with the present disclosure, the disclosed devices and methods provide for goggles that have ventilation holes disposed around the mounting surface of the goggle frame to which a goggle seal is attached. Ventilations holes disposed in such an arrangement provide for less restricted airflow between the seal of the safety goggles and the external environment. The additional airflow provided for by the ventilation holes creates an additional pathway for moisture to leave and dry the seal of the safety goggles and is configured to keep the interior volume of the safety goggles drier during use. The resulting reduction in moisture in the sealing component of the goggle reduces moisture in the air volume of the goggle thereby reducing condensation on the lens and thus improves optical clarity provided by the goggle as compared to traditional ventilation techniques. Embodiments consistent with the present disclosure involve an arrangement of the goggle's perimeter ventilating surfaces that allow airflow through the surface on which a sealing component of the goggle is attached.

BRIEF DESCRIPTION OF THE DRAWINGS

The present disclosure can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

As used herein, the term goggle means eyewear that includes side shields and otherwise protects a user's eyes from glare, dust, water, and other potential contaminates present in the environment. The term goggle can include sportswear goggles, such as goggles used in recreational activities such as snowboarding, skiing, motorcycle riding, snowmobile riding, cycling, and the like. The term goggle also includes eyewear used in industrial, medical, and laboratory settings. In addition, the term goggle can include eyewear configured to provide virtual reality (VR), augmented reality (AR), and/or extended reality (XR) features to a user of the eyewear (e.g., an entertainment goggle). The disclosed embodiments provide improvements to any such goggle by reducing condensation and improving optical clarity by providing a path for moisture to exit the seal of the goggle and pass into the surrounding environment.

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of apparatuses and methods consistent with aspects related to the invention as recited in the appended claims. Particular aspects of the present disclosure are described in greater detail below.

Figure 1:
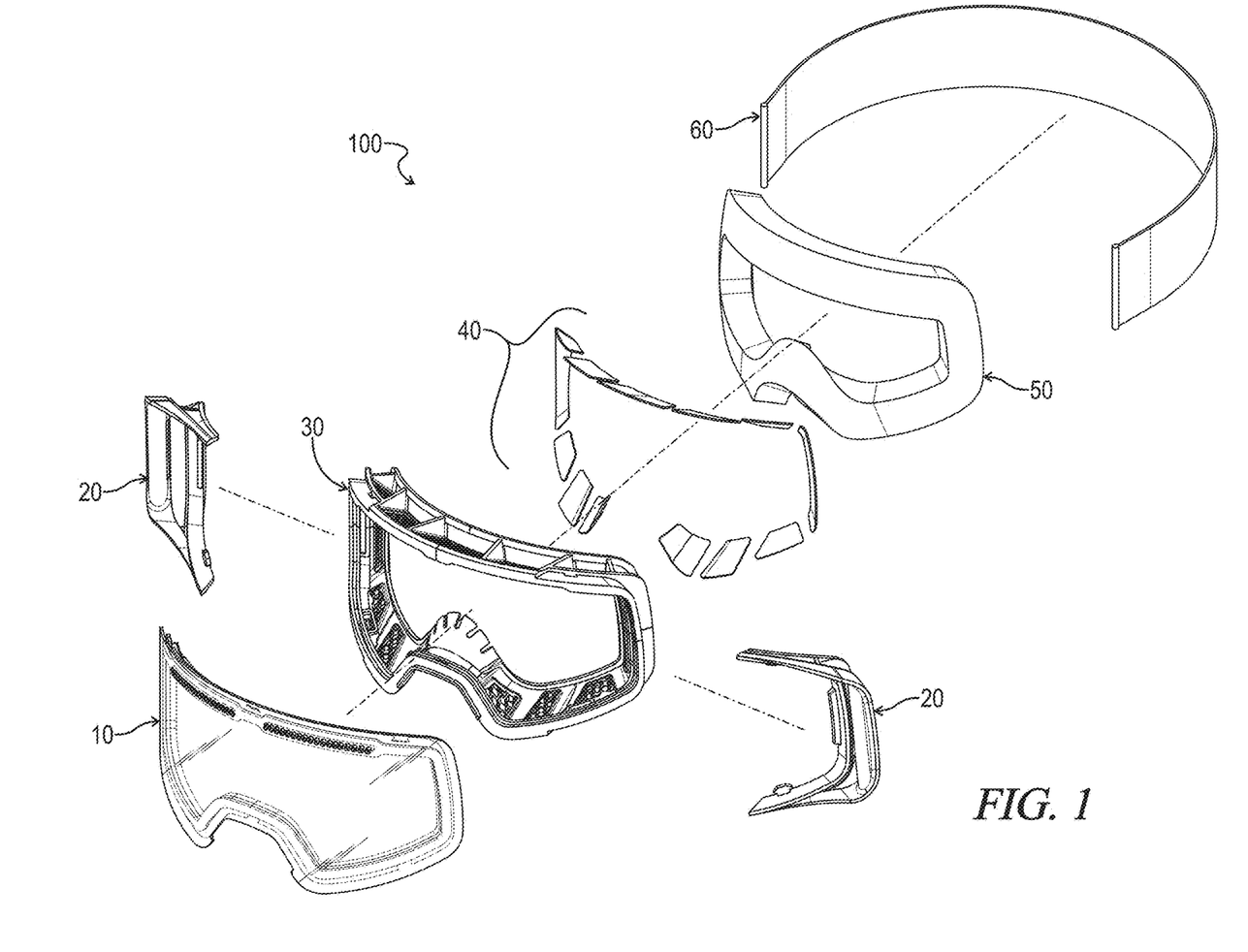
FIG. 1 is an exploded perspective view of a safety goggle, according to aspects of the present disclosure.

FIG. 1 depicts an exploded perspective view of exemplary goggle 100. Goggle 100 can include a lens 10, frame 30, insert 40, sealing component 50, strap 60, and strap attachment components 20. The lens 10 is configured to securely mount to frame 30 at a lens mounting surface 30B (see FIG. 4) via tabs, clips, or fasteners (not shown). In some examples, the lens 10 can be magnetically attached to the frame to allow a user of goggle 100 to rapidly swap lens 10 to another lens as desired. In some embodiments, the frame 30 can be of unitary construction, while in other embodiments, the frame 30 can be constructed from multiple pieces.

Notably, and as will be described in more detail with respect to FIGS. 2-6, frame 30 includes multiple apertures 32, 34, and 36 which provide a path through which moisture and condensation can be removed and dried from the sealing component 50 of the goggle and allowed to pass into the external environment. Apertures 32, 34, and 36 thereby can reduce moisture entering the internal volume of goggle 100 (defined as the space between the lens 10 and the face of the user, enclosed by the goggle frame 30 and sealing component 50). Notably, apertures 32, 34, and 36 are disposed through the sealing mounting surface 30A of frame 30 and directly interface with the sealing component 50 (see FIG. 2). Apertures 32, 34, and 36 therefore provide a direct path of air exchange between sealing component 50 and the external environment, thereby allowing moisture and condensation built up within sealing component 50 to more freely pass into the external environment. Thus, the arrangement of apertures 32, 34, and 36 provide for improved ventilation and removal of moisture and condensation from the internal volume of goggle 100 and the external environment as compared to traditional ventilation schemes utilized in goggles. In some embodiments, lens 10 can be treated with or constructed out of materials that prevent fogging/moisture buildup. For example, lens 10 can be constructed of a hydrophobic material or be treated with a hydrophobic film that prevents fogging of goggle 100.

Figure 2:
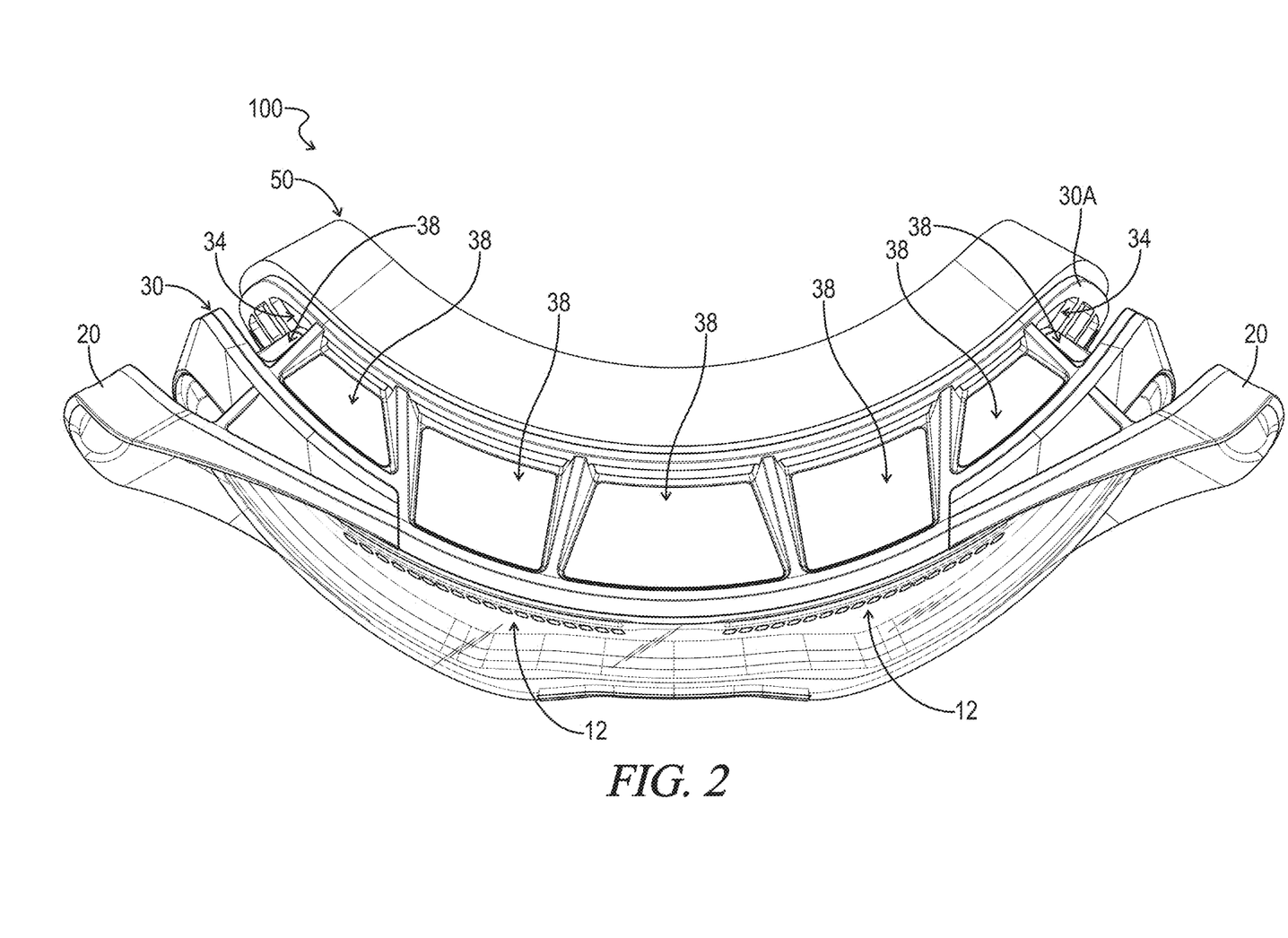
FIG. 2 is a top view of a safety goggle, according to aspects of the present disclosure.

Insert 40 can be of unitary construction in some embodiments. In other embodiments, insert 40 can comprise multiple pieces. In any case, insert 40 is configured to cover circumferential apertures (e.g., apertures 38 as shown in FIG. 2) present within frame 30. In some embodiments, insert 40 can be constructed of a permeable material, allowing for air, condensation, and moisture exchange between the internal volume defined by the goggle 100 and the user's face and the external environment through insert 40. In some embodiments, the insert 40 can be constructed of a semi-permeable material, allowing for some air, condensation, and moisture exchange between the internal volume defined by goggle 100 and the user's face and the external environment through insert 40. In some embodiments, the insert 40 can be constructed of a foam material, for example, an open cell, reticulated polyether foam, a fabric mesh or a micron mesh. Other materials may be used that provide sufficient air exchange between the internal volume of the goggle 100 and the external environment. In some embodiments, insert 40 may cover only some of the apertures present within goggle 100, while in other embodiments, insert 40 may be omitted entirely. In some embodiments, the frame 30 can be designed with an integrated venting structure (not shown) to support venting materials that may be used to further prevent water, mud, dust, insects, etc. from entering the internal volume of the goggle.

Strap 60 can be adjustable in length to fit a variety of head sizes and shapes. Strap 60 can be constructed of a durable, elastic material for the comfort of the user. In some embodiments, strap 60 is configured to attach directly to frame 30 of goggle 100. In other embodiments, goggle 100 can include strap attachment components 20 which function to attach strap 60 to frame 30. In some embodiments, strap attachments components 20 can be of unitary construction with frame 30. In yet other embodiments, strap attachment components 20 can be separate components that attach to frame 30 via various fastening means, such as detachable clips, tabs, or fasteners (not shown).

Sealing component 50 is configured to attach to frame 30 via various means. In some embodiments, sealing component 50 is attached to frame 30 via an adhesive. In some embodiments, sealing component 50 is attached to frame 30 via clips, buttons, snaps and/or hook and loop fasteners (e.g., Velcro™). In some embodiments, sealing component 50 can be perforated to improve air and moisture exchange between the user and the external environment. Sealing component 50 is configured to interface with frame 30 via sealing mounting surface 30A (see FIG. 2), while the opposite side of sealing component 50 is shaped and configured to comfortably interface with the face of a user of goggle 100 during wear. Sealing component 50 can be constructed of a variety of materials. In some embodiments, sealing component 50 can be constructed of a permeable or semi-permeable foam material that allow for air, condensation, and/or moisture exchange therethrough, which facilitates the exchange of air, moisture, and/or condensation between the sealing component 50 of goggle 100 and the external environment during use. In this regard, sealing component 50 can be constructed of an open cell, reticulated polyether foam. Yet other materials are envisioned for sealing component 50. In some embodiments, sealing component 50 can be of unitary construction. In yet other embodiments, sealing component 50 can be constructed of multiple pieces. In some embodiments, sealing component 50 can be of unitary construction with frame 30. For example, an additive printing process (e.g., 3D printing) can be used to construct a google with an integrated frame 30 and sealing component 50. Any type of material with suitable permeability and ability to seal against the face of a user can be used to construct sealing component 50. Notably, sealing mounting surface 30A is perpendicular or angled to the face of the user when goggles 100 are in a worn configuration and additionally sealing mounting surface 30A is also perpendicular or angled to the direction of airflow from an external environment, thereby maximizing airflow through sealing component 50 via the one or more apertures 32, 34, and 36.

FIG. 2 is a top view of safety goggle 100. As shown, frame 30 is connected to strap attachment components 20. Insert 40 is shown covering respective circumferential apertures 38. Circumferential apertures 38, unlike apertures 32, 34, 36 are typical of traditional goggles and provide ventilation between the internal volume of goggle 100 and the external environment, but do not provide the additional benefit of directly ventilating sealing component 50 that is provided by apertures 32, 34, and 36. Circumferential apertures 38 can vary in number, size, and shape as desired. Circumferential apertures 38 and lens apertures 12 can help warmer moister air to exit the internal volume defined by goggle 100. However, in some embodiments, goggle 100 may lack circumferential apertures 38 and lens apertures 12. For example, in some embodiment, circumferential apertures 38 can be disposed around the entire perimeter of frame 30. FIG. 2 additionally illustrates side apertures 34 arranged through sealing mounting surface 30A to which sealing component 50 is attached. Although FIG. 2 depicts four side apertures 34 though sealing mounting surface 30A on each side of goggle 100, the number, size, and arrangement of apertures 34 can be varied as desired. The arrangement of side apertures 34 directly against sealing component 50 facilitates the exchange of moisture collected within sealing component 50 with the external environment, which improves breathability of goggle 100 and reduces the amount of moisture and/or condensation that remains within the sealing component 50 of goggle 100 during use. Apertures 32, 34, and 36 are configured to provide enhanced airflow and exchange of condensation/moisture between the sealing component 50 of goggle 100 and the external environment by providing a direct path of air exchange between sealing component 50 and the external environment, thereby reducing moisture in the internal volume of the goggle 100 and improving optical clarity and reducing likelihood of fogging of lens 10. Conventionally, goggles fog as a result of heat and moisture that occurs from physical exertion of a user. Embodiments consistent with the present disclosure include apertures 32, 34, and 36 that can prevent fogging of goggles 100 by allowing for exchange of heat and moisture from the sealing component 50 of goggle 100 to the outside environment. In addition, by virtue of the positioning of apertures 32, 34, and 36 on the sealing mounting surface 30A and against the sealing component 50, any moisture that has wicked into sealing component 50 is dried via airflow through the apertures 32, 34, and 36. In comparison to conventional venting, such as circumferential apertures 38, apertures 32, 34, and 36 are positioned on the sealing mounting surface 30A of sealing component 50, which facilitates airflow while goggles 100 are in use. Air from the external environment moves in a direction into the sealing mounting surface 30A while goggles 100 are in a worn configuration, which can maximize the air exchange through apertures 32, 34, 36, sealing mounting surface 30A, and through sealing component 50. While sealing components of conventional goggles are known to have issues with the sealing component absorbing excess moisture generated by the user during physical exertion, apertures 32, 34, and 36 can reduce the wetting by providing direct airflow to sealing component 50 as described above.

As noted previously, insert 40 may be of unitary construction that fits around frame 30 and is configured to cover apertures 38, while in other embodiments insert 40 may be constructed of multiple components that respectively cover apertures 38. It should also be noted that in some embodiments, inserts 40 can be omitted entirely. Insert 40 is constructed such that it prevents debris and other environmental contaminates from entering the internal volume of goggle 100 to protect a user's face and eyes while still allowing the easy exchange of moisture, air, and/or condensation between the internal volume of goggle 100 and the external environment.

Figure 3:
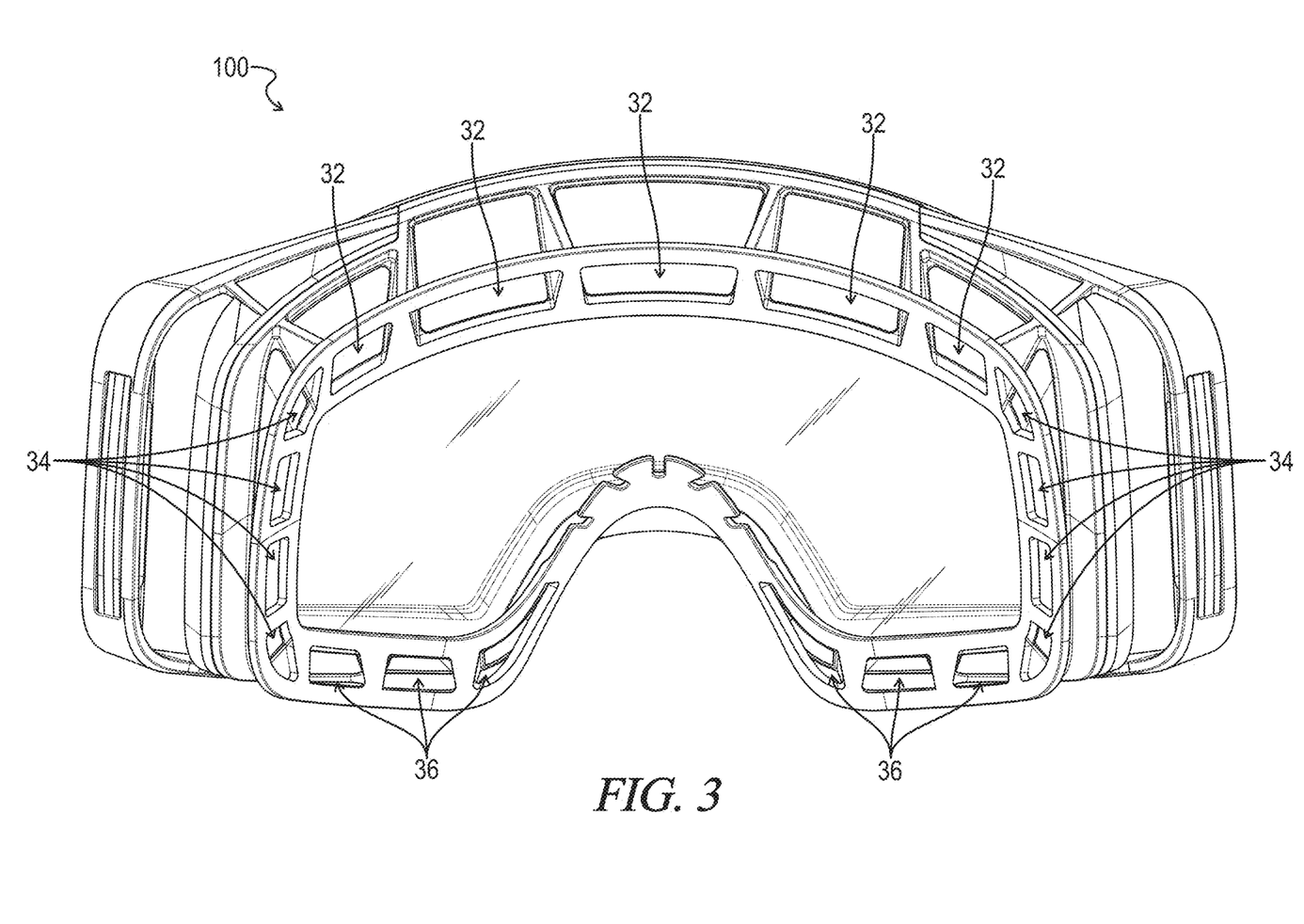
FIG. 3 is a cutaway view of a safety goggle, according to aspects of the present disclosure.

FIG. 3 is a cutaway view of safety goggle 100. As shown in FIG. 3, frame 30 can include a plurality of apertures 32, 34, and 36 that are disposed on the sealing mounting surface 30A of frame 30 to which sealing component 50 is attached. By providing apertures 32, 34, and 36 on the sealing mounting surface 30A, air, condensation, and/or moisture exchange is facilitated between the sealing component 50 of goggle 100 and the external environment when goggle 100 is in use. In the embodiment shown in FIG. 3, frame 30 includes side apertures 34, top apertures 32, and bottom apertures 36. It should be understood that in various embodiments consistent with the present disclosure, the number of apertures 32, 34, 36 can be varied and is not limited to the number of apertures 32, 34, 36 shown in FIG. 3. In some embodiments, certain illustrated apertures (e.g., one or more of apertures 32, 34, 36) can be omitted from frame 30. In some embodiments, additional apertures not illustrated in FIG. 3 can be included through sealing mounting surface 30A of frame 30 of goggle 100. It should also be understood that the size, shape, and positioning of apertures 32, 34, 36 can be varied as desired. Goggle 100 provides an advantage over previous devices by providing apertures 32, 34, 36 that allow for more effective air, moisture, and/or condensation exchange between the sealing component 50 of goggle 100 during wear and the external environment by providing a direct path for moisture and condensation to exit sealing component 50 into the external environment. It should be understood that apertures 32, 34, 36 can be configured to cover any or all of the sealing mounting surface 30A of frame 30 to which the sealing component 50 is attached.

Figure 4:
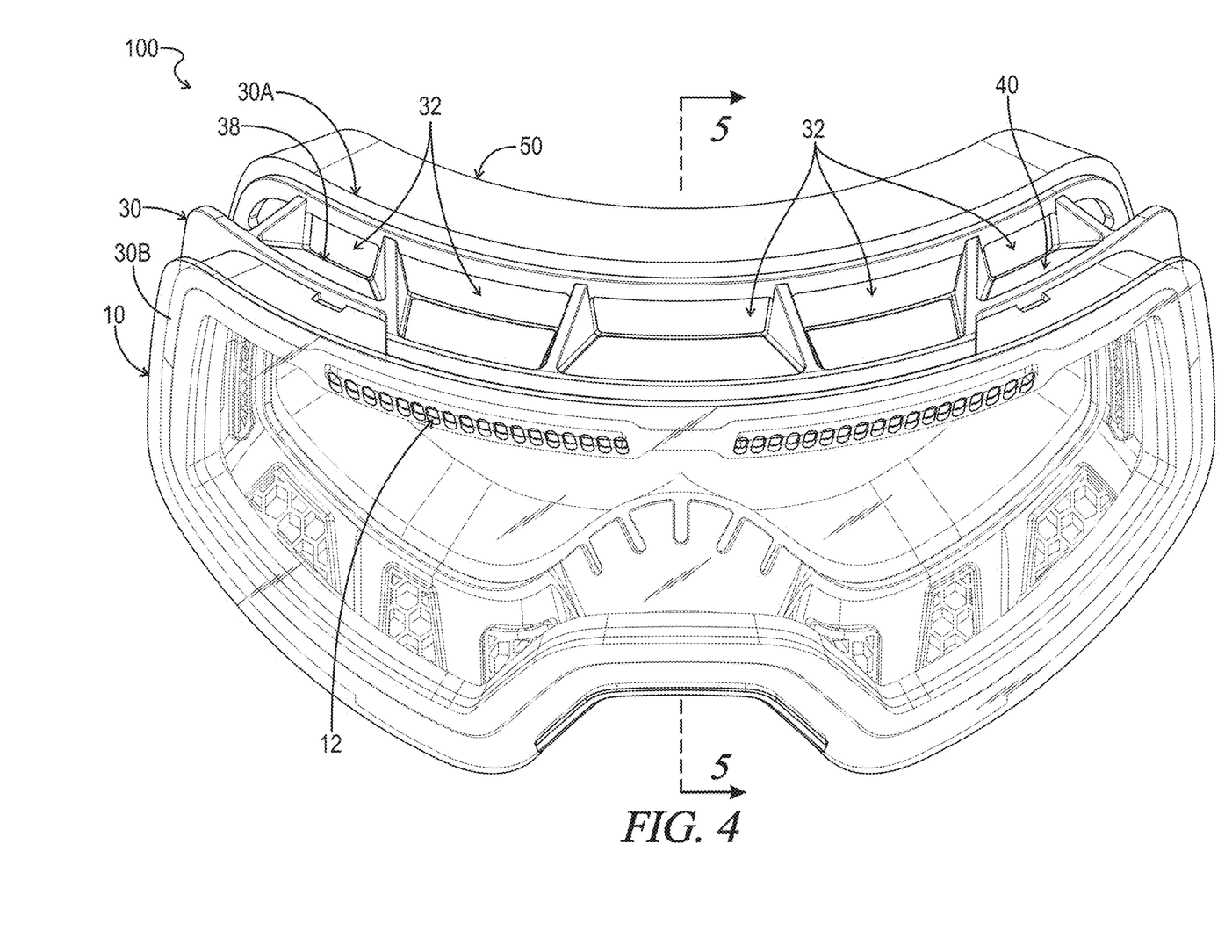
FIG. 4 is a top front perspective view of a safety goggle, according to aspects of the present disclosure.

FIG. 4 is a top front perspective view of safety goggle 100. As previously described with respect to FIG. 2, FIG. 4 shows insert 40 covering respective circumferential apertures 38. FIG. 4 also depicts top apertures 32 through sealing mounting surface 30A of frame 30. As described previously, top apertures 32 provide for a direct ventilation path through the sealing component 50, which allows moisture to be wicked away from sealing component 50 into the external environment more efficiently. Lens 10 is depicted having one or more lens apertures 12. Lens apertures 12 can be disposed through the lens 10 as desired to provide additional ventilation between the internal volume of goggle 100 during use and the external environment, similar to the function of circumferential apertures 38. Lens apertures 12 can be of varied size, shape, and placement through lens 10. Lens apertures 12 can be sized to prevent debris from entering into the internal volume of goggle 100 from the external environment while still providing for an effective means of air, condensation, and/or moisture exchange between the internal volume of goggle 100 and the external environment. It should be understood that in some embodiments, the number of lens apertures 12 within lens 10 can be varied, and in yet other embodiments, lens apertures 12 can be omitted entirely from the lens 10. As shown in FIG. 4, lens 10 can be mounted to frame 30 via lens mounting surface 30B, which is positioned opposite the sealing mounting surface 30A of frame 30.

Figure 5:
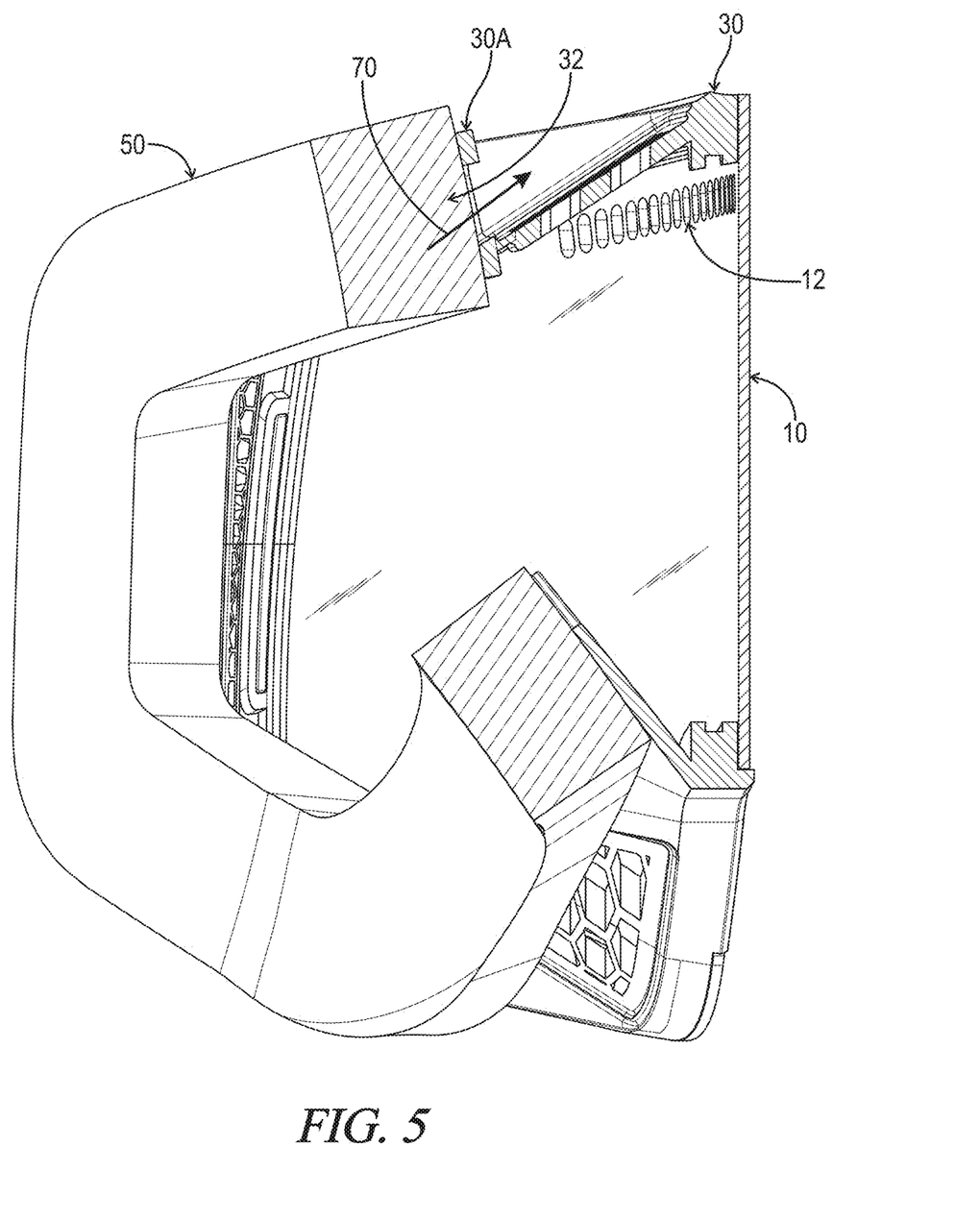
FIG. 5 is a section view of a safety goggle, according to aspects of the present disclosure.

FIG. 5 is a section view of safety goggle 100 taken along 5-5 as shown in FIG. 4. As shown in FIG. 5, goggle 100 can include apertures (e.g., aperture 32 as shown) that provide ventilation through the sealing mounting surface 30A to which sealing component 50 is attached. As compared to circumferential apertures 38 and/or lens apertures 12, apertures 32, 34, 36 provide the additional benefit of directly ventilating sealing component 50, which can build up with undesirable condensation and/or moisture which can create fogging within goggle 100 during use. By providing apertures 32, 34, 36 through sealing mounting surface 30A, the buildup of moisture within sealing component is substantially reduced, thereby reducing moisture in the internal volume of the goggle and improving optical clarity of goggle 100. Additional ventilation between the internal volume of the goggle 100 and the external environment can be provided via lens apertures 12 which can be disposed through the lens 10 as desired. In FIG. 5, arrow 70 shows the direction that moisture and excess heat can travel through the sealing component 50 and exit via an aperture 32. A similar arrow to 70 showing the direction that moisture and excess heat can travel through the sealing component 50 can be drawn with respect to apertures 34 and 36. It should also be understood that cooler, less moist air can also enter goggle 100 through the apertures 32, 34, 36 and into sealing component 50. For example, cooler and less moist air can move in a direction opposite arrow 70 into goggle 100 through apertures 32, 34, and 36 and sealing component 50.

In a conventional goggle, once the sealing component (e.g., sealing component 50) is wetted from sweat, that heat and moisture lingers in the internal volume of the goggle. In some embodiments consistent with the present disclosure, the goggle 100 prevents heat and moisture from wetting the sealing component 50 of the goggle 100. Apertures 32, 34, and 36 also help to dry the sweat in the sealing component 50 which allows the goggle to "recover" from periods of high moisture and heat generated by the activity of the wearer of goggle 100. By continuously moving moisture out of the sealing component 50, instances of higher perspiration and environmental moisture can be better absorbed by the sealing component 50. The reduced moisture in the sealing component 50 additionally improves the permeability of the sealing component 50 and contributes to an improved air exchange from the internal volume of the goggle 100 to the exterior environment. The improved air exchange reduces moisture in the goggle 100 that can condensate on the lens 10 surface, improving optical clarity for a user.

Figure 6:
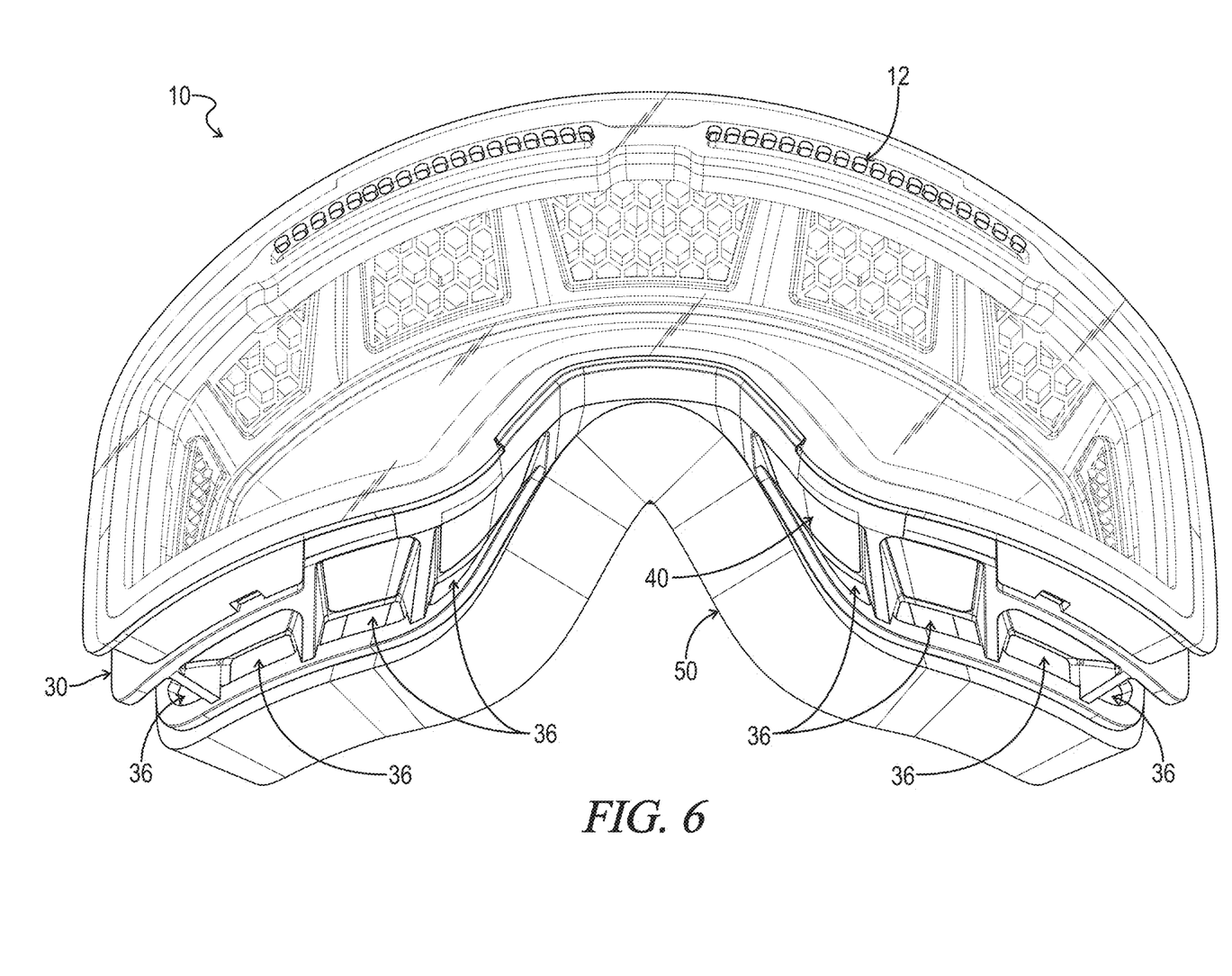
FIG. 6 is a rear front perspective view of a safety goggle, according to aspects of the present disclosure.

FIG. 6 is a rear front perspective view of safety goggle 100. FIG. 6 shows apertures 36 located on a bottom side of sealing mounting surface 30A to which sealing component 50 is attached. Insert 40 is shown that are covering respective circumferential apertures 38. Although in the embodiment shown in FIG. 6 there are four apertures 36 on either side of goggle 100 for a total of eight apertures 36, the size, number, and positioning of apertures 36 can be varied as desired.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process parameters (e.g., dimensions, configurations, components, process step order, etc.) may be made to further optimize the provided structures, devices, and methods, as shown and described herein. In any event, the structures and devices, as well as the associated methods, described herein have many applications. Therefore, the disclosed subject matter should not be limited to any single embodiment described herein, but rather should be construed in breadth and scope in accordance with the appended claims.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5%, and still more preferably within 1% of a given value or range of values. Numerical quantities given in this description are approximate unless stated otherwise, meaning that the term "about" or "approximately" can be inferred when not expressly stated.

With reference to the use of the word(s) "comprise," "comprises," and "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "including" should be interpreted to mean "including but not limited to . . . " unless the context clearly indicates otherwise.

The term "consisting essentially of" means that, in addition to the recited elements, what is claimed may also contain other elements (steps, structures, ingredients, components, etc.) that do not adversely affect the operability of what is claimed for its intended purpose. Such addition of other elements that do not adversely affect the operability of what is claimed for its intended purpose would not constitute a material change in the basic and novel characteristics of what is claimed.

The term "adapted to" means designed or configured to accomplish the specified objective, not simply able to be made to accomplish the specified objective.

The term "capable of" means able to be made to accomplish the specified objective.

The terminology used herein is for the purpose of describing particular embodiments only and is not intended to be limiting. As used herein, the singular forms "a", "an" and "the" are intended to include the plural forms as well (i.e., "at least one"), unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Terms such as "at least one of A and B" should be understood to mean "only A, only B, or both A and B." The same construction should be applied to longer list (e.g., "at least one of A, B, and C").

What is claimed is:
1. A goggle, comprising:
a frame having a sealing mounting surface;
a lens attached to the frame; and
a sealing component directly attached to the sealing mounting surface and configured to seal against a face of a user, wherein a space between the lens and the face of the user defines an interior volume of the goggle;
wherein the frame comprises a plurality of apertures extending through the sealing mounting surface, each aperture of the plurality of apertures forming a direct path of air exchange between the sealing component and an external environment for providing ventilation through the sealing component of the goggle and into the external environment, wherein the plurality of apertures includes side apertures extending through opposing side portions of the frame, top apertures extending through a top portion of the frame and bottom apertures extending through a bottom portion of the frame, the bottom portion of the frame being opposite the top portion of the frame and extending to and between the opposing side portions, wherein the frame includes a lens mounting surface to which the lens is attached and wherein the plurality of apertures do not extend through the lens mounting surface.

2. The goggle of claim 1, wherein the plurality of apertures are disposed between the external environment and the sealing component and reduce moisture in the sealing component.

3. The goggle of claim 1, wherein the sealing component comprises a permeable material.

4. The goggle of claim 3, wherein the permeable material comprises an open cell, reticulated polyether foam.

5. The goggle of claim 1, wherein the goggle is selected from a motorcycle goggle, a cycling goggle, a snow sports goggle, a medical goggle, a laboratory goggle, a safety goggle, an entertainment goggle, and a sports goggle.

6. The goggle of claim 1, wherein the sealing component is perforated.

7. The goggle of claim 1, further comprising a strap configured to secure the goggle to the face of the user and strap connection components attached to either side of the frame and configured to attach the strap to the frame.

8. The goggle of claim 1, further comprising one or more inserts configured to cover the plurality of apertures.

9. The goggle of claim 8, wherein the one or more inserts comprise an open cell, reticulated polyether foam.

10. The goggle of claim 1, wherein the lens further comprises one or more lens apertures.

11. A goggle, comprising:
a frame comprising a sealing mounting surface and a lens mounting surface opposite the sealing mounting surface and a plurality of apertures through the sealing mounting surface, wherein the plurality of apertures do not extend through the lens mounting surface;
a lens attached to the frame at the lens mounting surface; and
a sealing component attached to the frame at the sealing mounting surface and configured to seal against a face of a user, wherein the plurality of apertures provide for air exchange between the sealing component and an external environment,
wherein the frame includes opposing side portions, a top portion that extends to and between the opposing side portions and a lower portion, opposite the top portion, that extends to and between the opposing side portions,
wherein the plurality of apertures includes a first set of apertures that extends through the lower portion of the frame, each aperture of which forms a direct path of air exchange between the sealing component and the external environment.

12. The goggle of claim 11, wherein the sealing mounting surface is perpendicular or angled to the direction of air exchange when the goggle is in a worn configuration, thereby facilitating air exchange with the external environment through the plurality of apertures.

13. The goggle of claim 11, wherein the sealing component is selected from a permeable material and a semi-permeable material.

14. The goggle of claim 11, wherein the sealing component comprises an open cell, reticulated polyether foam.

15. The goggle of claim 11, wherein the goggle is selected from a motorcycle goggle, a cycling goggle and a snow sports goggle, a medical goggle, a laboratory goggle, a safety goggle, an entertainment goggle, and a sports goggle.

16. The goggle of claim 11, wherein the plurality of apertures include side apertures extending through the opposing side portions of the frame, and top apertures extending through the top portion of the frame.

17. The goggle of claim 11, further comprising a strap configured to secure the goggle to the face of the user and strap connection components attached to either side of the frame and configured to attach the strap to the frame.

18. The goggle of claim 11, further comprising one or more inserts configured to cover the plurality of apertures.

19. The goggle of claim 18, wherein the one or more inserts comprise a material selected from a permeable material and a semi-permeable material.

20. The goggle of claim 18, wherein the one or more inserts comprise an open cell, reticulated polyether foam.

21. The goggle of claim 11, wherein the lens further comprises one or more lens apertures.

22. A goggle, comprising:
a frame including first portion forming a sealing mounting surface, a second portion forming a lens mounting surface, a third portion extending to and between the first portion and the second portion, a plurality of first apertures extending through the sealing mounting surface, and a plurality of second apertures extending through the third portion;
a lens attached to the frame at the lens mounting surface; and
a sealing component attached to the frame at the sealing mounting surface and configured to seal against a face of a user,
wherein the plurality of first apertures form paths for air exchange between the sealing component and an external environment and the plurality of second apertures form paths for air exchange between a space between the lens and the face of the user and the external environment, and
wherein the paths for air exchange between the sealing component and the external environment do not extend through any of the second portion, the third portion and the lens mounting surface.

23. The goggle of claim 22, wherein first portion extends from the third portion to form a flange through which the plurality of first apertures extend.

* * * * *